(12) United States Patent
Wanderman

(10) Patent No.: US 10,172,748 B1
(45) Date of Patent: Jan. 8, 2019

(54) INVERTING DIGIT BANDAGE WITH DEPLOYMENT STRIPS

(71) Applicant: First Freedom Financial, Inc, Grand Cayman (KY)

(72) Inventor: Steven Wanderman, Sedona, AZ (US)

(73) Assignee: FIRST FREEDOM FINANCIAL, INC (KY)

( * ) Notice: Subject to any disclaimer, the term of this patent is extended or adjusted under 35 U.S.C. 154(b) by 0 days.

(21) Appl. No.: 15/687,496

(22) Filed: Aug. 27, 2017

(51) Int. Cl.
*A61F 15/00* (2006.01)
*A61F 13/02* (2006.01)
*A61F 13/10* (2006.01)
*A61F 13/00* (2006.01)

(52) U.S. Cl.
CPC ........ *A61F 15/005* (2013.01); *A61F 13/0206* (2013.01); *A61F 13/0266* (2013.01); *A61F 13/105* (2013.01); *A61F 2013/00093* (2013.01); *A61F 2013/00119* (2013.01)

(58) Field of Classification Search
CPC ...... A61F 15/005; A61F 13/10; A61F 13/104; A61F 13/105; A61F 5/11; A61F 13/102; A61F 2006/044; A61F 2006/047; A61F 2006/049; A61B 46/27
See application file for complete search history.

(56) References Cited

U.S. PATENT DOCUMENTS

| 2,068,703 | A |  | 1/1937 | Powdermaker |
| 2,646,796 | A |  | 2/1950 | Scholl |
| 2,522,842 | A |  | 9/1950 | Scholl |
| 2,712,313 | A |  | 7/1955 | Levy |
| 2,875,758 | A |  | 3/1959 | Boles et al. |
| 2,969,144 | A |  | 1/1961 | Zachheim |
| 3,934,582 | A | * | 1/1976 | Gorrie .............. A61B 46/27 602/62 |
| 4,926,851 | A |  | 5/1990 | Bulley |
| 5,012,801 | A |  | 5/1991 | Feret |
| 5,181,914 | A | * | 1/1993 | Zook .............. A61F 13/105 128/888 |
| 5,643,189 | A |  | 7/1997 | Maini |
| 6,139,514 | A | * | 10/2000 | Benson ............ A61F 13/105 602/22 |
| 6,482,491 | B1 |  | 11/2002 | Samuelsen et al. |
| 7,316,034 | B1 |  | 1/2008 | Berry et al. |

(Continued)

FOREIGN PATENT DOCUMENTS

| GB | 887165 A | 1/1962 |
| GB | 1490065 A | 10/1977 |

*Primary Examiner* — Peter S Vasat
(74) *Attorney, Agent, or Firm* — Invention To Patent Services; Alex Hobson

(57) ABSTRACT

An inverting digit bandage system enables covering a digit, such as a finger or toe, with an inverting digit bandage by pulling deployment strips. An inverting digit bandage has a sleeve portion that is rolled up into a toroid portion along with the deployment strip, A deployment tab extends from the deployment toroid and pulling down on the deployment tab unfurls the inverting digit bandage over a digit. An attachment tab may be configured on the extended end of the sleeve and have an adhesive to secure the bandage over the digit. The deployment strip may be attached to a release layer configured over the adhesive on the attachment tab and may remove the release layer when pulled from the inverting digit bandage.

21 Claims, 15 Drawing Sheets

(56) References Cited

U.S. PATENT DOCUMENTS

| | | |
|---|---|---|
| 7,779,483 B2 | 8/2010 | Berry et al. |
| 8,822,751 B2 | 9/2014 | Gajiwala |
| 2004/0267226 A1 | 12/2004 | Dabi et al. |
| 2011/0030697 A1* | 2/2011 | Thompson ................ A61F 6/04 128/844 |
| 2016/0129229 A1* | 5/2016 | Pettygrove ............ A61M 35/00 604/307 |
| 2017/0087027 A1 | 3/2017 | Coffey et al. |
| 2017/0340486 A1* | 11/2017 | Hutchful ........... A61F 13/00059 |

* cited by examiner

INVERTING DIGIT BANDAGE WITH DEPLOYMENT STRIPS

BACKGROUND OF THE INVENTION

Field of the Invention

The invention is directed to an inverting digit bandage having deployment strips for unfurling the inverting digit bandage over a digit, such as a finger or toe, wherein the inverting digit bandage can be self-applied in a sterile manner without contamination and provide uniform compression to the entire digit.

Background

Fingers and toes are often subjected to trauma resulting in lacerations, abrasions, and other soft tissue injuries requiring the application of a bandage. Digits are notorious for the difficulty encountered during wound coverage due to the inherent limitations that current bandages offer. That is, despite the availability of a myriad of bandage sizes and shapes, there often persists an issue with conformity due to the varied anatomy and size of both fingers and toes. Furthermore, maintenance of coverage with bandages including the need for frequent reapplication due to unexpected loosening is often necessary to effectuate continuous coverage and thereby maintain a clean wound with optimization of healing. The inherent limitations of non-conforming bandages and in particular, the difficulty utilizing sterile techniques during application is readily apparent when attempting to place a bandage on one's own finger. Most bandages provide optimal coverage when applied to the midsection of a digit, but fail to adequately conform and adhere to the more distal, non-linear aspects of the digit. Fingertip injuries are unfortunately a frequent site of trauma resulting in abrasions, lacerations, partial amputations and open crush injuries. In addition, bandages are frequently exposed to water due to the individuals washing of their hands, the holding of sweating beverage containers, and the like. A wet bandage is prone to accelerated loosening which may increase susceptibility to secondary infection once the sterile field is violated. In addition, contamination of a typical bandage may occur simply during removal from its packaging or by its application with unclean hands. And last, the standard strip-type bandage does not provide uniform compression of a digit which can result in a tourniquet-like effect causing significant swelling distal to the bandage as well as an increased risk for neurovascular compromise. Both may adversely affect healing and a satisfactory outcome.

SUMMARY OF THE INVENTION

The invention is directed to an inverting digit bandage system comprising an inverting digit bandage that is unfurled and inverts as it extends down over a digit, such as a finger or toe. An exemplary inverting digit bandage system comprises a deployment strip that is rolled up with the sleeve portion of the inverting digit bandage and that when pulled unfurls the sleeve portion over the shaft of the digit. An exemplary inverting digit bandage may comprise an attachment tab that extends from the sleeve portion and comprises an attachment adhesive for adhering to the digit. A removable release layer may be configured over the attachment adhesive to prevent the attachment adhesive from adhering to other portions of the inverting digit bandage when in the deployment toroid. The deployment strips may be attached to the release layer and thereby allow removal of the release layer by simply pulling on the deployment strip. A single release layer may be attached to a single deployment strip or two or more release layers may be attached to separate deployment strips.

An exemplary inverting digit bandage is provided as a deployment toroid for covering a digit. An exemplary deployment toroid has a toroid portion which is the sleeve portion rolled up along with the deployment strip or strips and may include the attachment tab. A top portion of the inverting digit portion extends within the toroid portion, which has a toroid shape, and covers the top of the digit. This complete encapsulation of the digit, extending from the distal end of the digit to the base of the digit better protects the wound and may prevent or reduce contamination and loosening of the bandage, such as from washing your hands. An exemplary deployment toroid comprises one or more deployment tabs that extend out from the toroid portion. A deployment tab may be a piece of the deployment strip or may be looped to form a deployment loop. A person may insert a finger into a deployment loop to deploy the inverting digit bandage over a digit. By simply pulling down on the deployment strip, the toroid portion will be unfurled thereby covering the digit shaft with the sleeve portion. An exemplary inverting digit bandage may comprise one deployment strip or two, wherein the two deployment strips may be configured on opposing sides of the inverting digit bandage. An exemplary inverting digit bandage may be packaged in a sterile package and application without the need to touch the digit or internal surfaces of the bandage may maintain a sterile field on the wounded digit.

The inverting digit bandage may be provided in any number of sizes to accommodate the various types of digits and anatomical variances between people. An inverting digit bandage may have a length of about 1 cm or more, about 2 cm or more, about 4 cm or more, about 6 cm or more, about 8 cm or more and any length between and including the length values provided. A lesser toe may require a short inverting digit bandage, such as about 4 cm or less, and a middle or index finger may require a longer inverting digit bandage, such as about 6 cm or more. Likewise, the diameter of the sleeve or top portion of the inverting digit bandage may be provided in a variety of sizes, such as about 5 mm or more, about 10 mm or more, about 15 mm or more, about 25 mm or more about 30 mm or more and any size between and including the diameters provided. A thumb or great toe may require a larger diameter inverting digit bandage, such as about 20 mm or more, and a little finger or fifth toe may require a smaller diameter inverting digit bandage, such as about 20 mm or less.

Describing coverage of the wounds sustained by the digits of the hands and feet benefit by an understanding of their nomenclature. The digits of the hand and feet excluding the thumb and great toe each have 3 segments: proximal, middle and distal. The distal segments contain the nail plates. The thumb and great toe differ by their absence of a middle segment. Each digit has a dorsal and volar surface. The dorsal surface is synonymous with the "back" or "top" of the fingers and toes. Likewise, the volar surface equivalent is the palmar surface of the fingers and thumb and the plantar surface of the lesser toes and great toe. When a wound is sustained to a proximal segment of a digit, an exemplary inverting digit bandage must extend proximal enough to cover the entire wound and hence be selected based on its length to provide adequate coverage. In these cases, one or more discrete adhesive attachment tabs may extend further proximally from the sleeve end and adhere to the distal hand or distal foot proper. In an exemplary embodiment, an inverting digit bandage comprises two attachment tabs that are configured on opposing sides of the sleeve and these tabs may then be attached to the palmer and dorsal surfaces of a hand or the plantar and dorsal surfaces of the foot. The digit from the proximal to distal end is referred to herein as the digit shaft.

A wound may be located on any portion of a finger including any or all of the three segments such as the proximal segment, the distal segment, or the middle segment located between the proximal and distal segments. Furthermore, a wound may be localized to the palmer surface of the fingers, that is the same side as the palmer aspect of the hand, or the plantar surface of the toes, that is the same side as the plantar aspect of the foot. Likewise, a wound may be located on the dorsal aspect of the fingers and toes, that is, the backs of the fingers or the top of the toes, respectively. When a wound is configured on a proximal segment of a finger or toe, an exemplary inverting digit bandage that extends proximally over the wound with attachment tabs to the hand or foot proper may be selected to effectively cover the wound. In these cases, one or more discrete attachment tabs may extend from the sleeve end and proximally onto the hand or foot. In an exemplary embodiment, an inverting digit bandage comprises two attachment tabs that are configured on opposing sides of the sleeve portion and these tabs may be attached to the palmer and dorsal side of a hand or the plantar and dorsal side of the foot.

An exemplary inverting digit bandage comprises an absorbent layer that is configured on the inside of the inverting digit bandage for contact with the wound on the digit surface, or therapeutic location. An absorbent layer may comprise natural and/or synthetic materials or fabrics, such as cotton or non-woven bats of fibers. An antibiotic or therapeutic material may be configured with or coated on the absorbent layer. An absorbent layer may be any suitable thickness and various product may be provided for different types of wounds. A laceration or wound with excessive drainage including blood and/or purulent material may require a bandage with a thicker absorbent layer. In addition, an absorbent layer may contain a bacteriostatic or bactericidal substance including an antibiotic, for example. An absorbent layer may comprise a non-stick, coating or barrier material to prevent adhesion of the absorbent layer to the wound and may include a polymer screen or netting material.

An exemplary inverting digit bandage comprises a dressing layer that is configured on the outside of the inverting digit bandage to provide some protection of the absorbent layer. An exemplary dressing layer may be hydrophobic and prevent or reduce water from passing through to the absorbent layer. An exemplary dressing layer may be synthetic material and may stretch to allow the sleeve portion to be rolled into the toroid portion. An exemplary dressing layer may be elastic and stretch or elongate as the sleeve portion is rolled up into the toroid portion and then shrink back while the sleeve portion is unfurled over a digit. An elastic dressing layer may comprise vinyl, silicone, urethane or other elastomeric materials that exhibit dimensional recovery to substantially an original shape or dimension after deformation, such as by stretching. An exemplary elastic dressing layer will expand or stretch as it is rolled into the toroid portion and then may shrink back down as the toroid is unfurled. An exemplary dressing layer may be water-proof or water resistant and may comprise a hydrophobic material or coating. In an exemplary embodiment, a dressing layer is hydrophobic and breathable, comprising a polymer film that prevents water penetration but allows for gas to permeate therethrough.

An exemplary inverting digit bandage has an attachment tab that extends from the extended sleeve end and has an adhesive layer for adhering to the digit. An exemplary attachment tab may extend as a sleeve completely around the digit circumference or may be one or more discrete portions that extend only a portion around the circumference of the digit Two or more discrete attachment tabs may overlap to allow complete coverage around the circumference of the digit to form a sleeve from the two or more discrete attachment tabs. A release layer may be coupled over an attachment adhesive to prevent adhesion while in the deployment toroid form. An exemplary release layer may be a single continuous release layer or may comprise two or more discrete and separate release layers, each covering a portion of the attachment adhesive of the attachment tab. The release layer may be paper or a coated paper or film that prevents adhesive from passing through, but does not strongly attach to the adhesive. A release layer may comprise discontinuities to allow the release layer to be rolled into the toroid portion and discontinuities may be cuts or slits in the release layer. The release layer may extend out or around the extended end of the attachment tab. For example, the release layer may extend from the inside surface of the attachment tab, wherein it covers the attachment adhesive to the outside surface, around the extended end of the attachment tab. The release layer may be attached to the deployment strip thereby allowing the release layer to be removed by pulling on the deployment strip.

An exemplary method of inverting a bandage over a digit is provided herein. The method comprises the steps of providing an exemplary inverting digit bandage, as described in any of the embodiments herein. The method comprises placing the top portion of the deployment torpid over the extended distal end of a digit and then pulling on the deployment strip to unfurl and invert the sleeve portion over the digit. The method may further comprise the step of removing a release layer from an attachment tab and adhering the attachment adhesive to the digit to attach the inverting digit bandage to the digit. The release layer may be removed by pulling on the deployment strip wherein the deployment strip is attached to the release layer.

An exemplary inverting digit bandage provides a sterile means of application of the inverting digit bandage whereby excessive handling is not required. The inverting digit bandage requires little to no contact for application, whereby only the deployment tab or tabs are touched.

An exemplary inverting digit bandage provides uniform pressure/compression over a digit. Some digit injuries, such as the crush type injury, may cause significant swelling of the digit wherein application of a strip type bandage placed circumferentially around the digit may cause excessive compression beneath the bandage and increased swelling distal to the bandage due to a tourniquet-like affect of the strip type bandage. This may subsequently cause increased pain, neurovascular compromise and ultimately impair healing. An exemplary inverting digit bandage may be sized to provide uniform compression over the digit, thereby reducing swelling and pain and hence providing an improved physiologic environment for healing.

An exemplary method of making an exemplary inverting digit bandage, as described herein, includes forming the bandage on a form and then inverting over the deployment strip to locate the layers in the proper locations with respect to each other. A first form is used to prepare the elastic dressing and absorbent material. A dressing is applied over a first form. An adhesive may attach the dressing to the absorbent material or portion and this adhesive may by applied after the dressing is configured on the form. The dressing may extend further down the form than the absorbent material and this extended dressing portion may form a layer of the attachment tab. The dressing/absorbent material assembly is then inverted onto a second form having the deployment strip configured thereon. One or two deployment loops may be configured at the extended end of the second form and may be configured in a recessed portion of the form. A vacuum may be used to maintain the position of the deployment strip on the second form as the dressing/absorbent material assembly is inverted thereover. The extended end portion of the dressing, that is the segment which does not contain the absorbent layer, may now be rolled down or inverted and adhesive may be applied. The adhesive applied between the dressing portion and the absorbent material may extend down onto the exposed portion of the dressing portion. However a release sheet would be needed to prevent sticking of the adhesive as the dressing/absorbent material assembly is inverted onto the second form. The deployment strip and release layer are then coupled to the adhesive on the extended end of the dressing layer. The deployment strip may be discontinuous with the release layer or it may be a one-piece unit, wherein the release layer is in continuity with the extended end of the deployment strip. The assembly is now inverted to produce an inverting digit bandage having a deployment toroid, a top portion, and exposed deployment strips that may include a deployment loop or loops.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
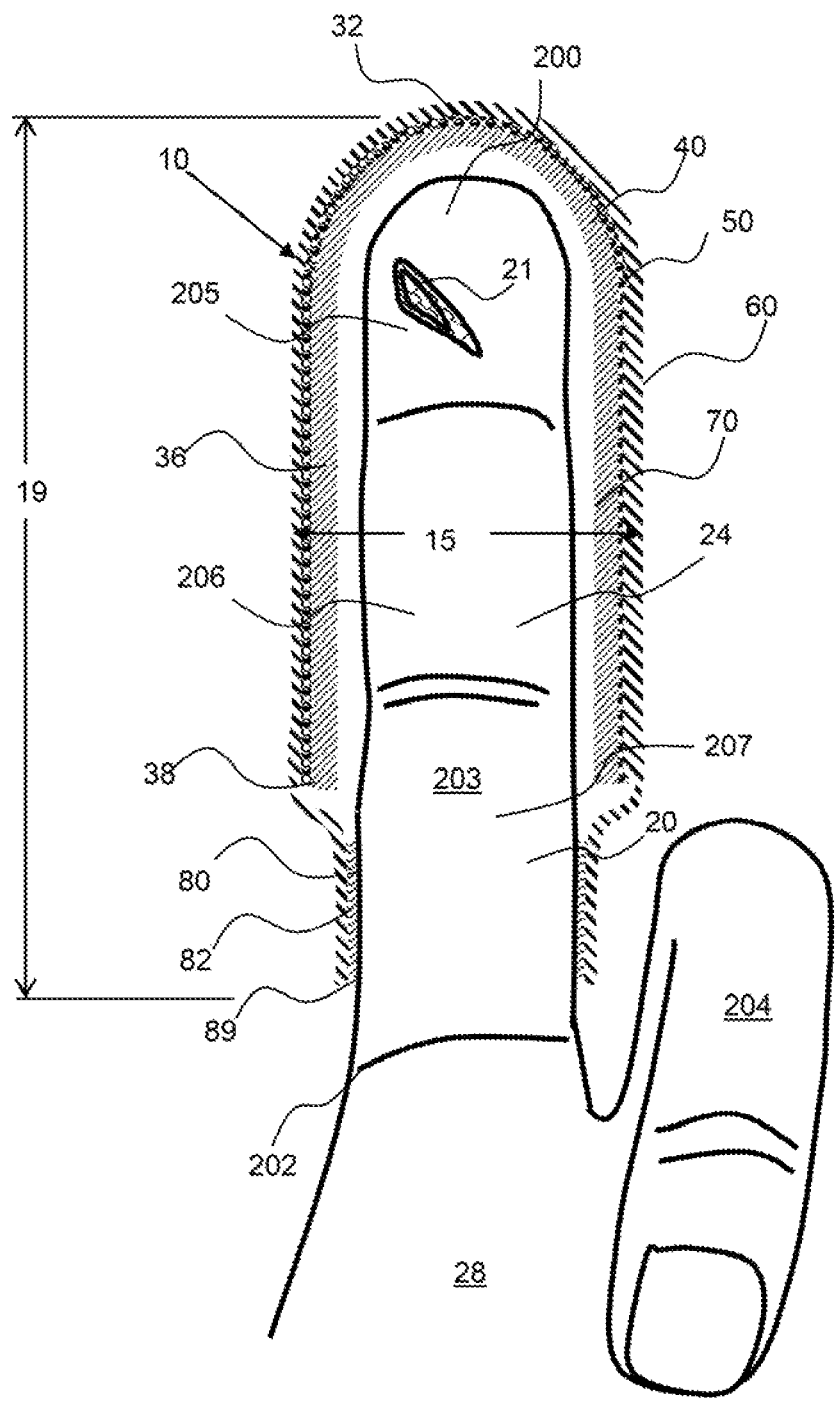
FIG. 1 shows a cross-section view of an exemplary inverting digit bandage configured over a person's index finger.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention, Other embodiments of the invention, and certain modifications, combinations and improvements of the described embodiments will occur to those skilled in the art and all such alternate embodiments, combinations, modification and improvements are within the scope of the present invention.

Definitions

Digit, as used herein, includes the fingers and thumb of the hand, and the lesser toes and great toe of the foot.

As shown in FIG. 1, an exemplary inverting digit bandage system 10 comprises an inverting digit bandage 30 that is configured over a person's finger, or digit 20. A wound 220 is in the distal segment 205 of the finger, however this exemplary inverting digit bandage would cover a wound in the middle segment 206. The wound is on the volar side 203 of the finger but would also cover a wound on the dorsal side 204 of the finger, as it encapsulates at least a portion of the finger. Each finger has a proximal segment 207, coupled to the hand 28, and a distal segment 205 on the distal end 200 of the digit 20. The top portion 32 of the inverting digit bandage is configured over the distal segment 205 of the digit, and the sleeve portion 36 is configured around the finger or digit 20, or digit shaft 24. The sleeve portion covers the distal segment 205 and the middle segment 206 of the digit 20. An attachment tab 80 extends from the sleeve end 38 toward the proximal end 202 of the digit 20. As described herein, the attachment tab may extend completely around the circumference of the digit and may be a sleeve or one or more attachment tabs may extend around a portion of the circumference of the digit shaft. The attachment tab comprises an attachment adhesive 82 that adheres to the person's finger or hand. The exemplary inverting digit bandage comprises an absorbent layer 40, a dressing layer 60 and attachments 50 therebetween. The exemplary inverting digit bandage may also comprise antibiotics or other therapeutic solutions 70. The exemplary inverting digit bandage has a length 19 and an outer diameter 15.

Figure 2:
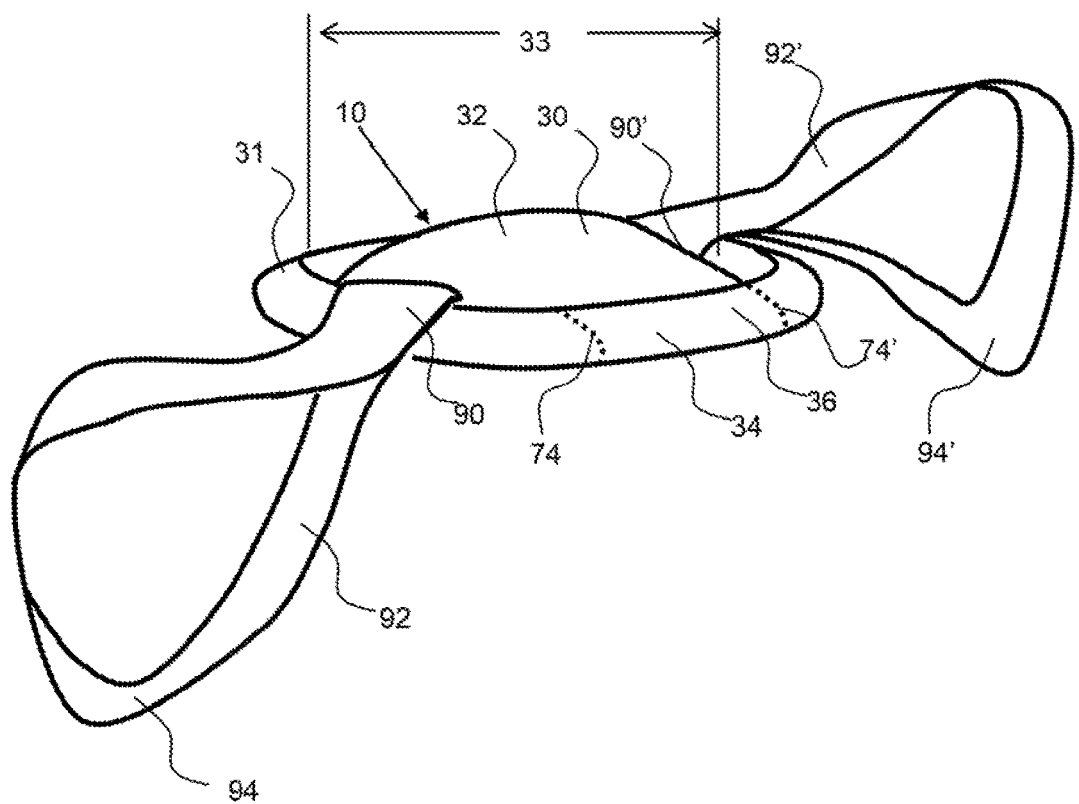
FIG. 2 shows a perspective view of an exemplary inverting digit bandage system, comprising a pair of deployment strips configured extending from the rolled-up sleeve portion of the inverting digit bandage.
Figure 8:
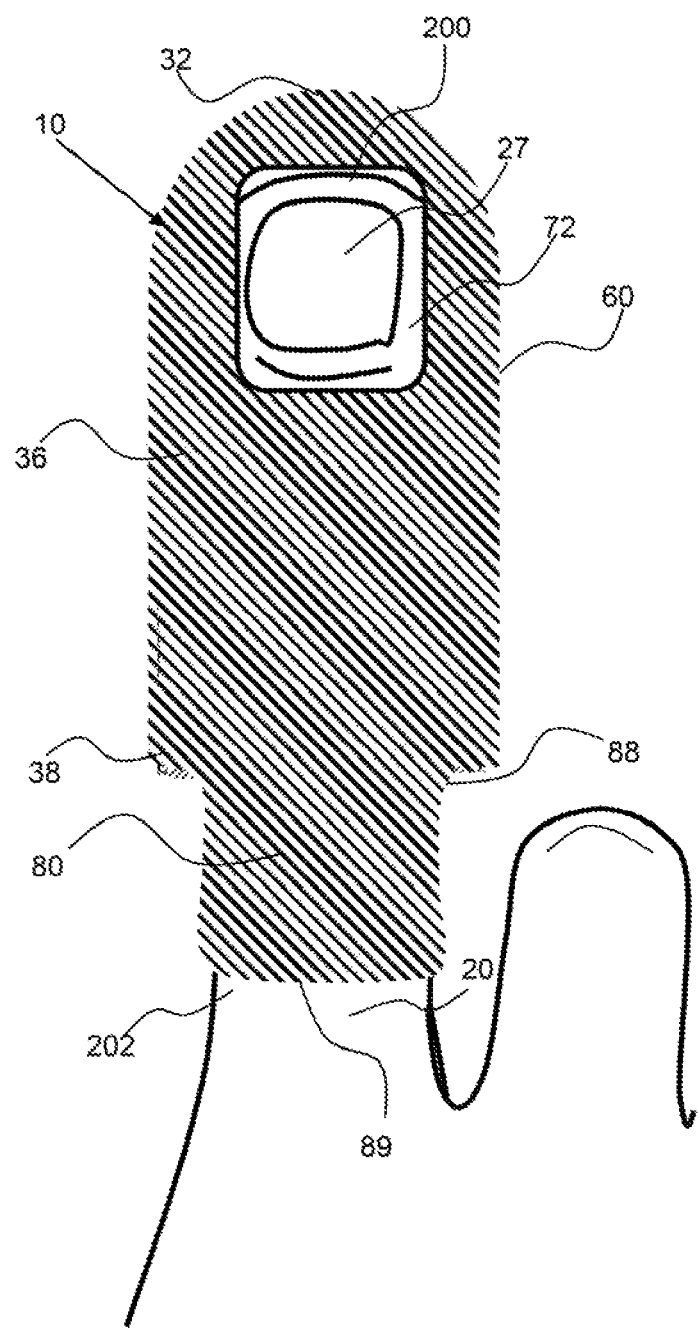
FIG. 8 shows an exemplary inverting digit bandage configured over a person's index finger with the attachment tab extending from the inverting digit bandage and attached to the proximal end of the person's index finger.

As shown in FIG. 2, an exemplary inverting digit bandage system 10 comprises a pair of deployment tabs 92, 92' that are deployment loops 94, 94' respectively, extending form the roiled-up sleeve portion 36 that now forms the toroid portion 34 of the deployment toroid 31. The deployment tabs are the extended end of the deployment strips 90, 90' respectively that are roiled-up in the toroid portion 34 along with the sleeve portion. The deployment tabs form deployment loops 94 that can be configured around a person's finger or fingers to deploy or unfurl the toroid portion into the sleeve portion over the digit. The deployment strips are adjacent to the dressing layer 60. The top portion 32 extends within the toroid portion and is configured to cover the tip or distal most surface of a digit. The top portion may also comprise an absorbent layer, a dressing layer and attachments therebetween, or may be some other material, such as only dressing material. The top portion has a diameter 33. Also shown in FIG. 2, are window markings 74, 74' that indicate the location of an inspection/viewing window 72, as shown in FIG. 8. The window markings enable a user to align the bandage before deployment, so that the viewing window is aligned over the nail of the digit.

Figure 3:
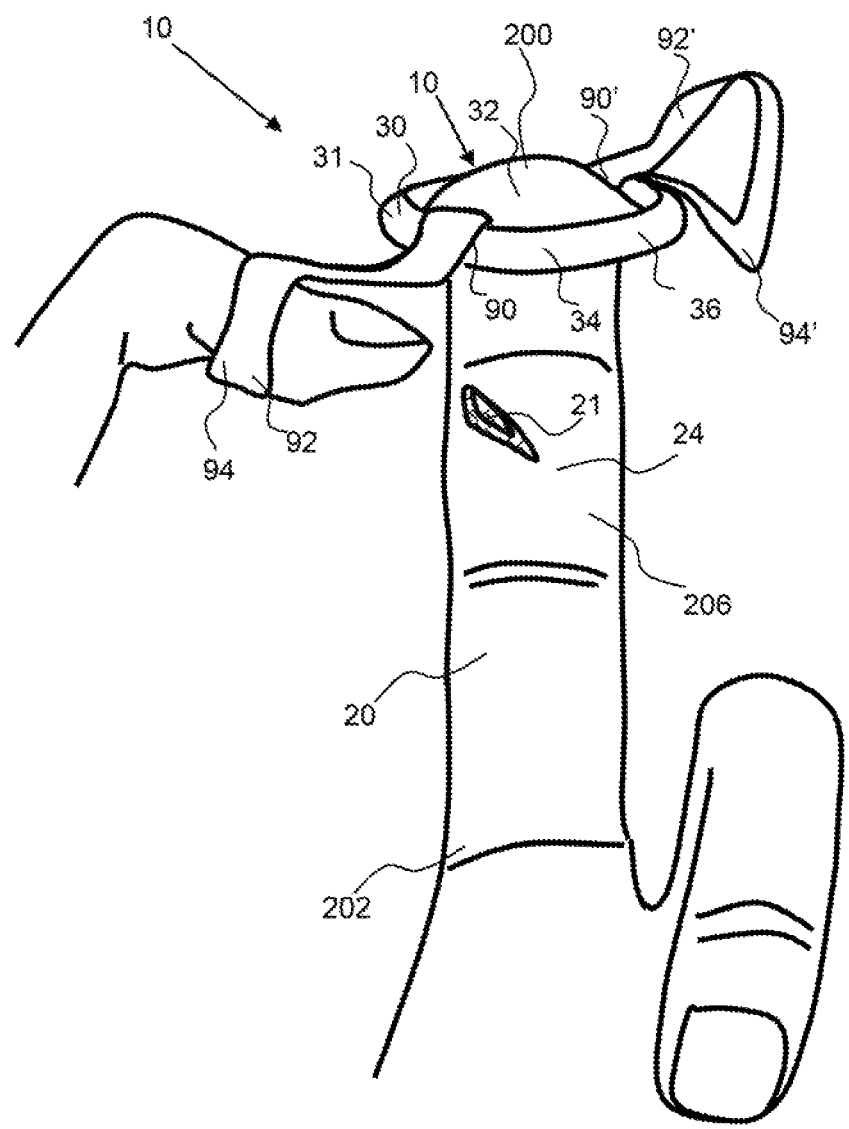
FIG. 3 shows an exemplary inverting digit bandage in a deployment toroid form configured over the distal end of a person's index finger with the top portion resting on the distal end of the finger and the toroid portion extending around the distal segment.

As shown in FIG. 3, the deployment toroid 31 is configured on the distal end 200 and a person has placed the deployment loop 94 over their finger. A person may use one or the pair of deployment loops 94, 94' to unfurl the inverting digit bandage 30 over the digit 20.

Figure 4:
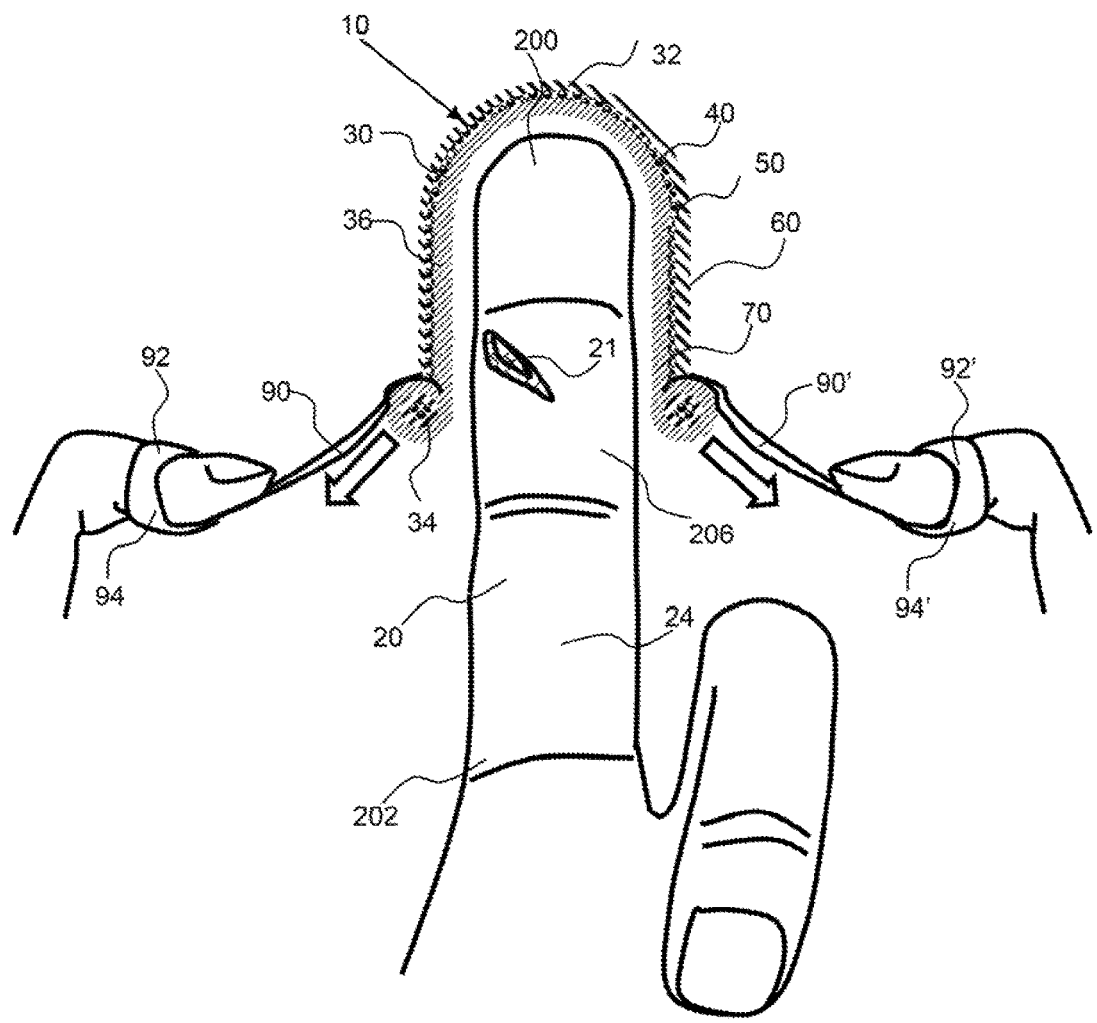
FIG. 4 shows a cross-section view of an exemplary inverting digit bandage configured over a person's index finger and being deployed by pulling on the deployment strips as the toroid portion is pulled down over the finger.

As shown in FIG. 4, an exemplary inverting digit bandage 30 is configured over a person's index finger, an exemplary digit 20, and is being deployed by pulling on the deployment strips 90, 90' as the toroid portion 34 is pulled down over the digit, or digit shaft 24. The deployment strips are rolled up within the toroid portion and as the deployment strips are pulled down, as indicated by the bold arrows, they deploy the sleeve portion 36 over the shaft of the finger, or digit shaft 24. Both deployment tabs are being used to deploy the inverting digit bandage 30.

Figure 5:
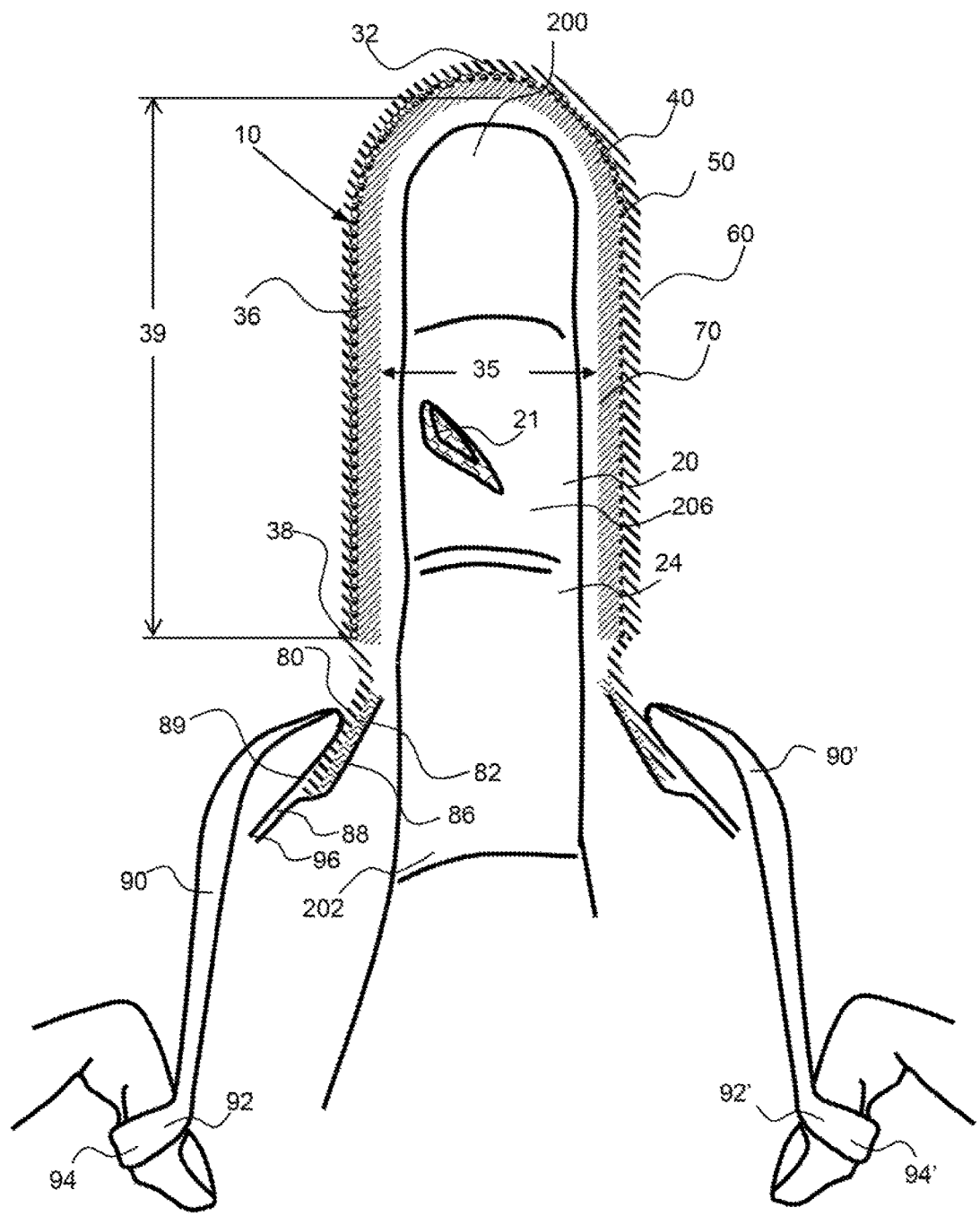
FIG. 5 shows a cross-section view of the exemplary embodiment inverting digit bandage shown in FIG. 4, now extended proximally down over the index finger with a pair of attachment tabs extending from the sleeve portion and the deployment strips attached thereto.

As shown in FIG. 5, an exemplary inverting digit bandage system 30 is configured over a person's index finger 20, an exemplary digit 20, and now extends down over the index finger with the sleeve portion 36 covering a portion of the digit shaft 24. A pair of attachment tabs 80, 80' are extending from the sleeve end 38 and the deployment strips 90, 90' are attached to the attachment tabs. As the deployment strip is pulled the attachment tabs are extended from the inverting digit bandage 30. The attachment tabs 80 extend to an extended end 88. A release layer 86 is configured on the inside surface of the attachment tab to prevent the attachment adhesive 82 from sticking to the sleeve portion 36 when rolled into the toroid portion. The release layer 86 extends past the extended end 89 of the attachment tab 80 and is attached to the deployment strip 90 by an attachment 88, such as an adhesive attachment. In this exemplary embodiment, the portion of the deployment strip proximal to the extended end 96 is attached to the release layer 86. The sleeve portion of the inverting digit bandage has a length 39 from the top portion 32 to the extended sleeve end 38, The sleeve portion has an inner diameter 35.

Figure 6:
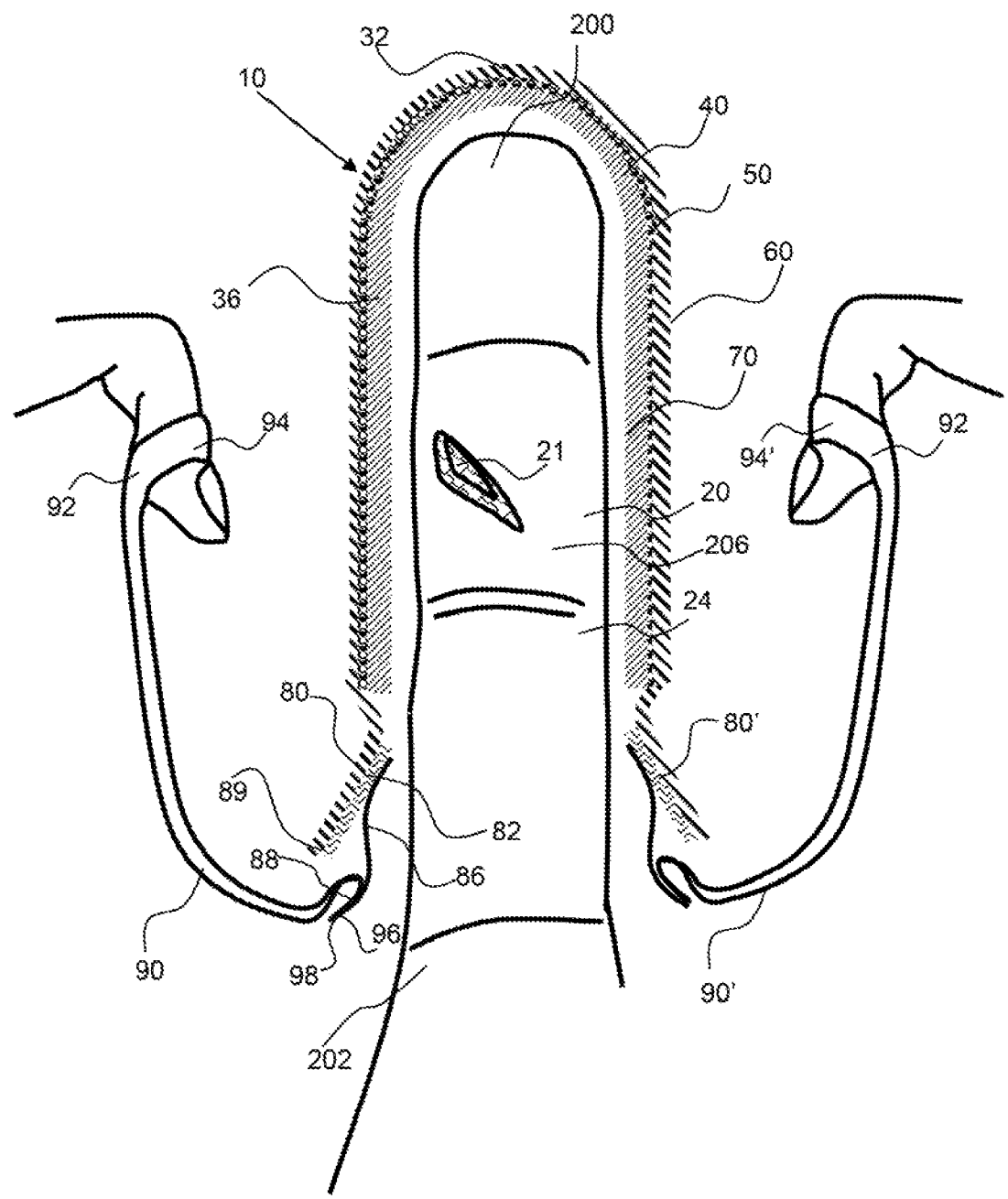
FIG. 6 shows a cross-section view of the exemplary inverting digit bandage shown in FIG. 5, with the deployment strips attached to a release layer configured over the attachment adhesive of the attachment tab.

As shown in FIG. 6, an exemplary inverting digit bandage 30 is configured over a person's finger, an exemplary digit 20, and the deployment strips 90, 90' are attached to a release layer 86 and, as the deployment strips are pulled, the release layer 86 is removed from the attachment tab 80.

Figure 7:
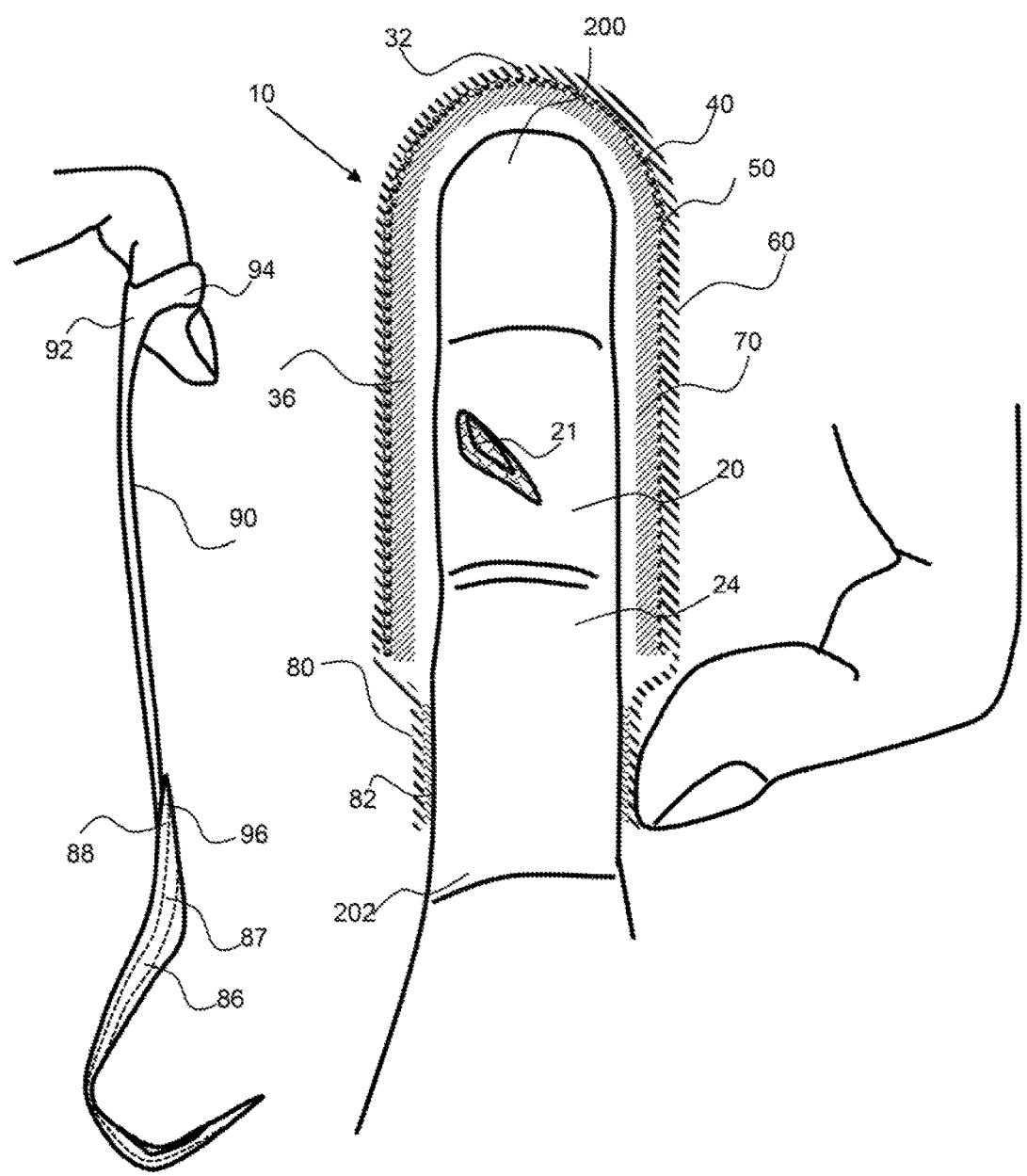
FIG. 7 shows a cross-section view of the exemplary embodiment inverting digit bandage shown in FIG. 6, with the deployment strip removed and pulling away the release layer and a person pressing the attachment tab to the person's finger.

As shown in FIG. 7, an exemplary inverting digit bandage 30 is configured over a person's finger, an exemplary digit 20, and the deployment strips 90 have removed the release layer 86 from the attachment tab 80 and is still attached to the deployment strip by a release layer attachment 98. The release layer comprises discontinuities 87 such as slits or perforations to allow the release layer to more easily be rolled into the toroid. The discontinuities may extend along the length of the release layer as shown. A person is pressing the attachment tab 80 to the person's finger 20 to adhere the attachment adhesive 82 to the digit 20 and thereby further securing and attaching the inverting digit bandage to the digit, or finger as shown.

As shown in FIG. 8, an exemplary inverting digit bandage system 10 comprises an inverting digit bandage 30 configured over a person's index finger, an exemplary digit 20, with the attachment tab 80 extending from the sleeve end 38 and attached to the proximal end 202 of the digit. The attachment tab extends from the attached portion 88 to the extended end 89. As shown in FIG. 8 an exemplary inverting digit bandage 30 comprises a viewing window 72. This viewing window, may be a cut-out area or non-coverage area of the bandage to allow inspection and diagnosis of a digit without removal of the bandage. A window may also comprise a transparent layer of material, such as a plastic film that enables inspection through the window but that prevents contamination of the wound and water from penetrating into the absorbent material. In an exemplary embodiment, the viewing window overlays a digit nail 27 A nail easily affords the ability to visualize the color of the nail plate which is representative of the skin perfusion and enables a capillary refill compression test. There may be a marking on the deployment toroid to indicate the location of the viewing window about the circumference of the deployment toroid, thereby allowing a user to align the inverting digit bandage before deployment. The use of the viewing window for inspection and diagnosis prevents frequent removal and replacement of bandages that can be painful, interfere with the healing, process and expose the wound and digit to contamination and the risk of infection.

Figure 9:
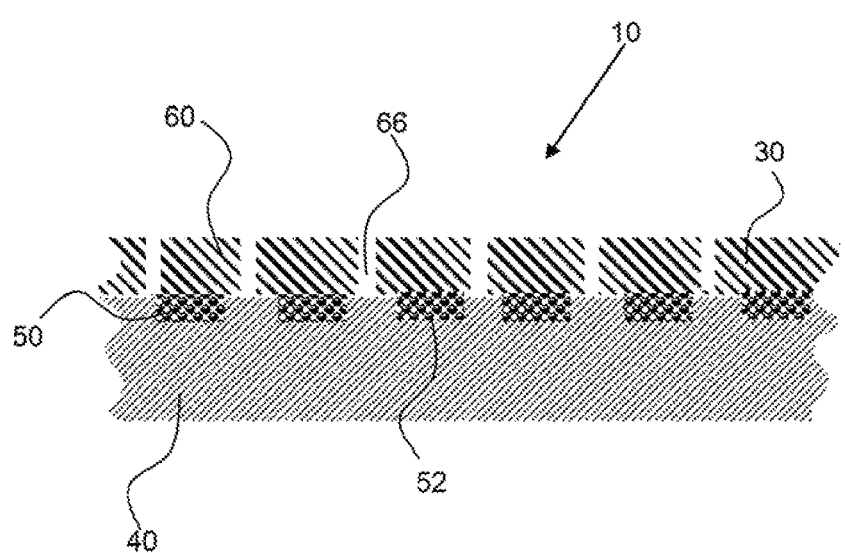
FIG. 9 shows a cross-section view of an exemplary inverting digit bandage having an absorbent layer, a dressing layer and an adhesive therebetween.

As shown in FIG. 9, an exemplary inverting digit bandage 30 comprises an absorbent layer 40, a dressing layer 60 and an attachment 50, such as an adhesive 52 therebetween. The dressing layer 60 comprises a plurality of apertures 66 to allow the bandage to breath.

Figure 10:
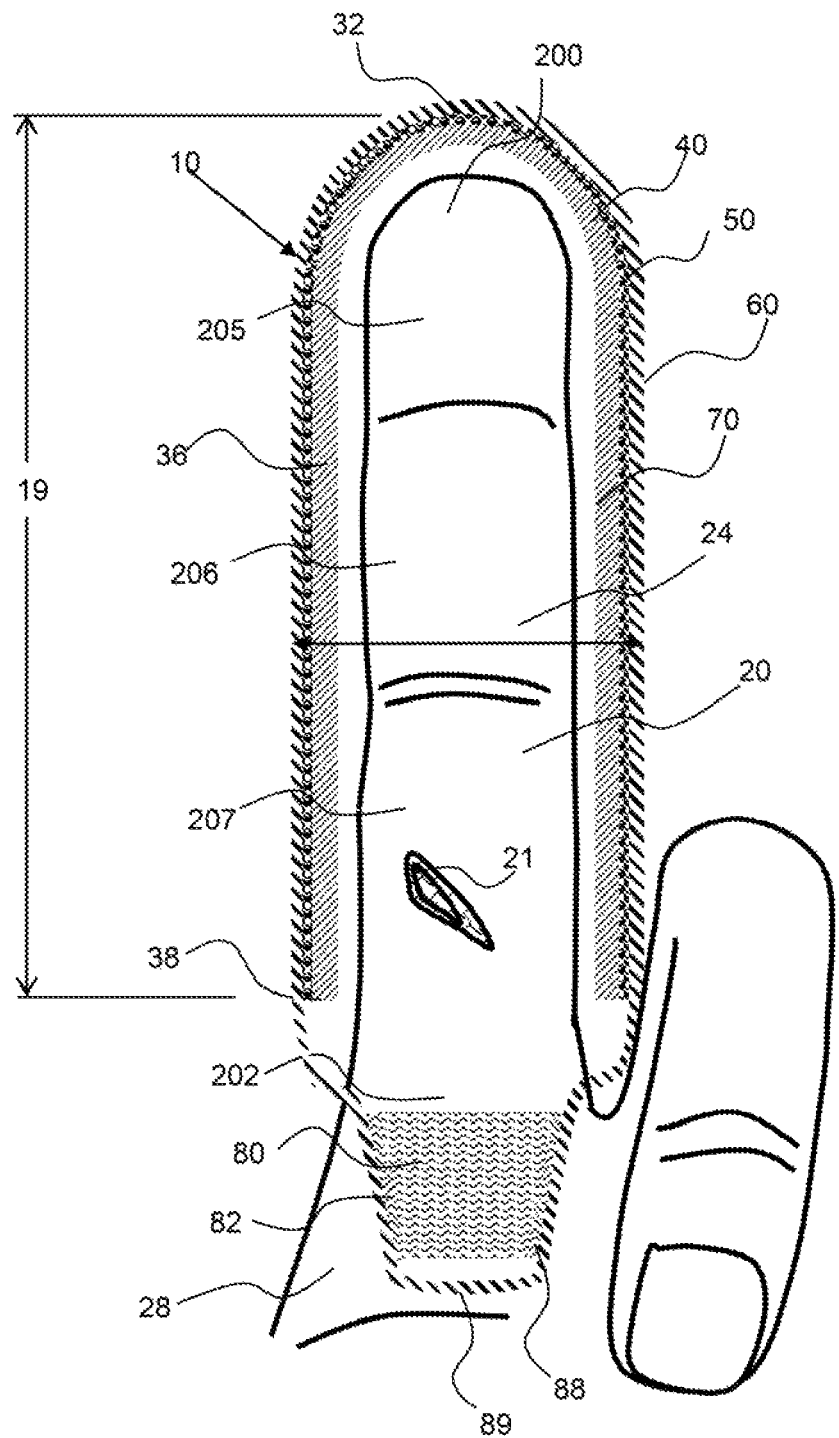
FIG. 10 shows a cross-section view of an exemplary inverting digit bandage configured over a person's index finger and attached to the hand by a discrete attachment tab.

As shown in FIG. 10, an exemplary inverting digit bandage system 10 comprises an inverting digit bandage 30 that is configured over a person's finger, or digit 20. The top portion 32 of the inverting digit bandage is configured over the digit fingertip 22, or distal end of the digit, and the sleeve portion 36 is configured around the finger or digit shaft 24. The sleeve portion 36 of the exemplary inverting digit bandage extends to the proximal end 202 of the digit shaft 24, and a discrete attachment tab 80 extends from the sleeve end 38 down onto the person's hand 28. The wound 21 is configured on the proximal segment of the finger requiring the sleeve portion to extend substantially over the entire length of the finger. The extended end 89 of the attachment tab 80 is on the palmer portion of the person's hand 28. There may be a second discrete attachment tab on the dorsal portion of the person's hand, not shown. The attachment tab comprises an attachment adhesive 82 that adheres to the person's hand. The exemplary inverting digit bandage comprises an absorbent layer 40, a dressing layer 60 and attachments 50 therebetween. The exemplary inverting digit bandage may also comprise antibiotics or other therapeutic solutions 70. The exemplary inverting digit bandage has a length 19 and an outer diameter 15.

Figure 11:
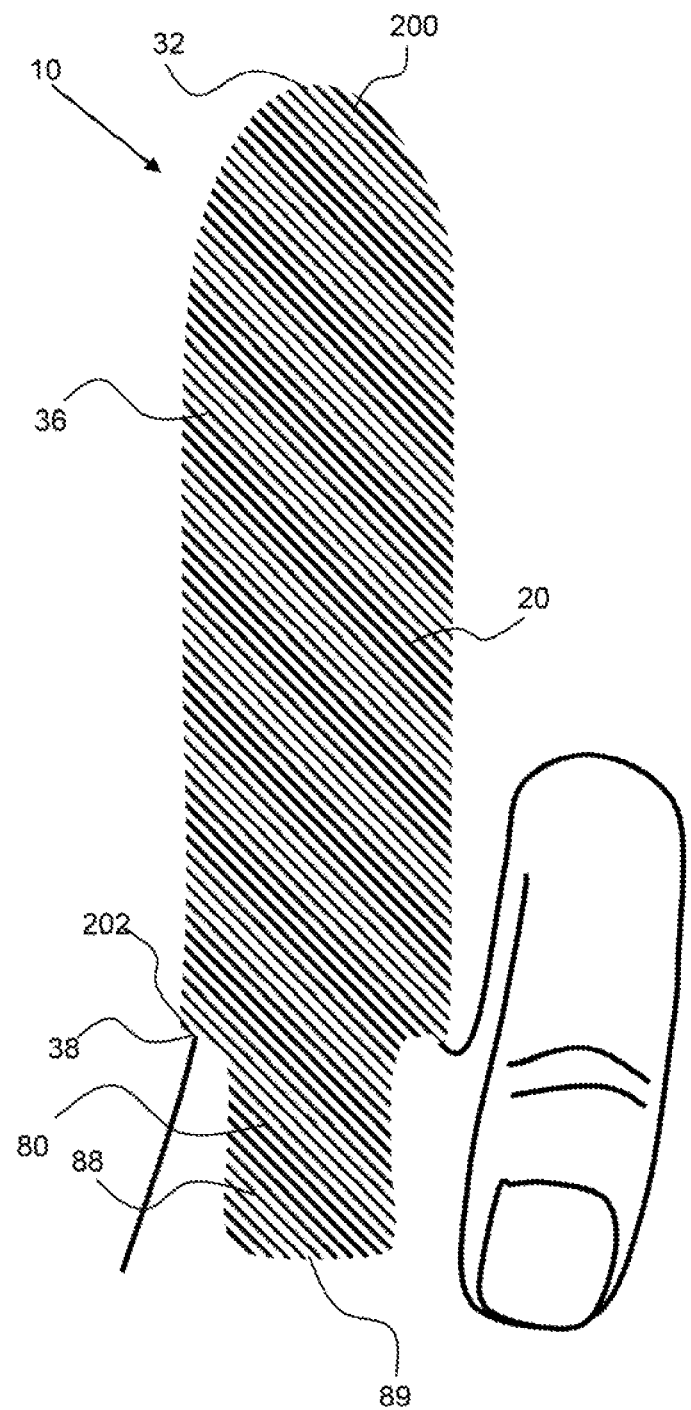
FIG. 11 shows an exemplary inverting digit bandage configured over a person's index finger with the attachment tab extending from the inverting digit bandage and attached to the hand adjacent to the proximal segment of the person's index finger.

As shown in FIG. 11, an exemplary inverting digit bandage system 10 comprises an inverting digit bandage 30 configured over substantially the person's index finger, wherein it covers the finger from the proximal segment to the digit fingertip, or distal end of the finger. A discrete attachment tab 80 is extending from the sleeve end 38 and is attached to the person's hand. The attachment tab extends from the attached portion 88 to the extended end 89.

Figure 12:
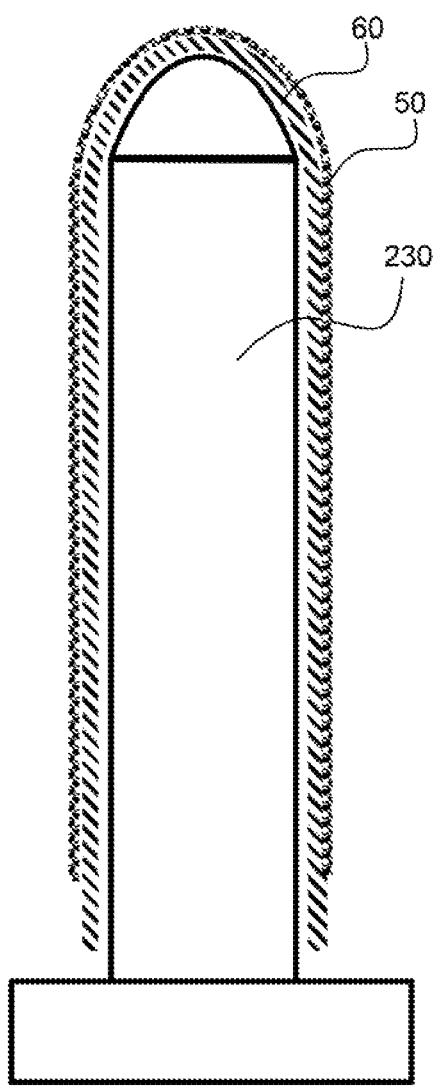
FIGS. 12 to 17 show a method of making an exemplary inverting digit bandage.
Figure 13:
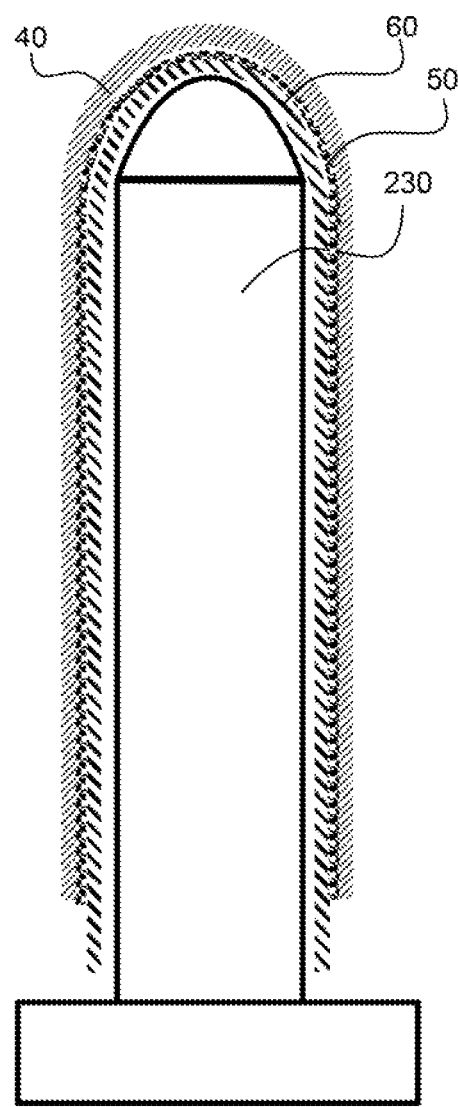
Figure 14:
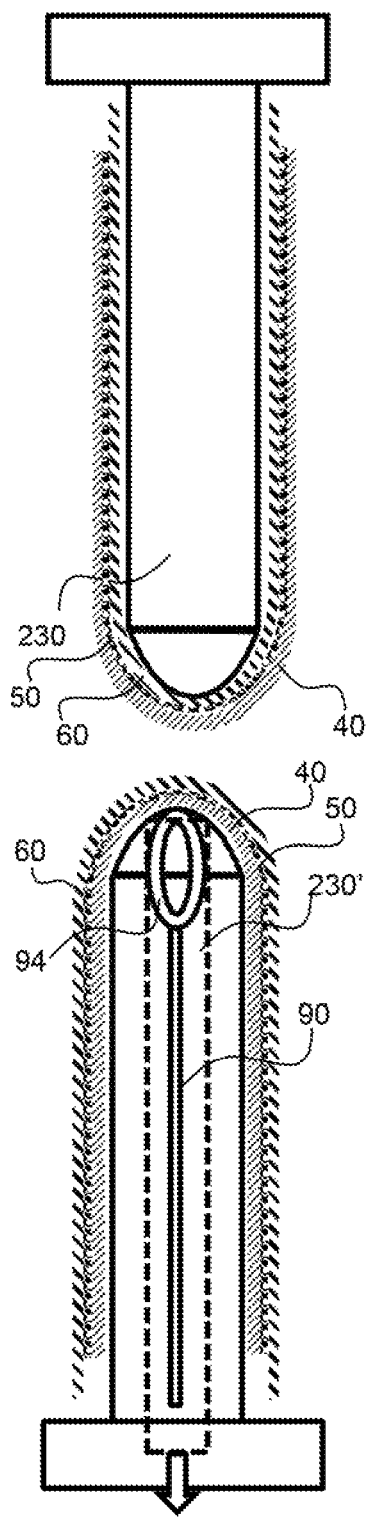
Figure 15:
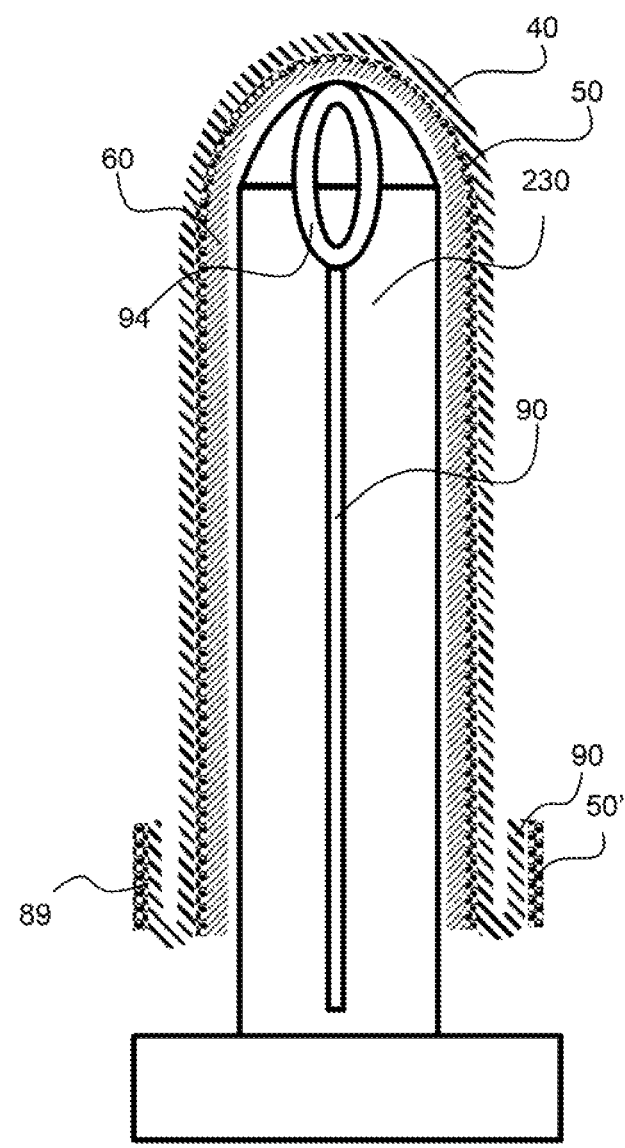
Figure 16:
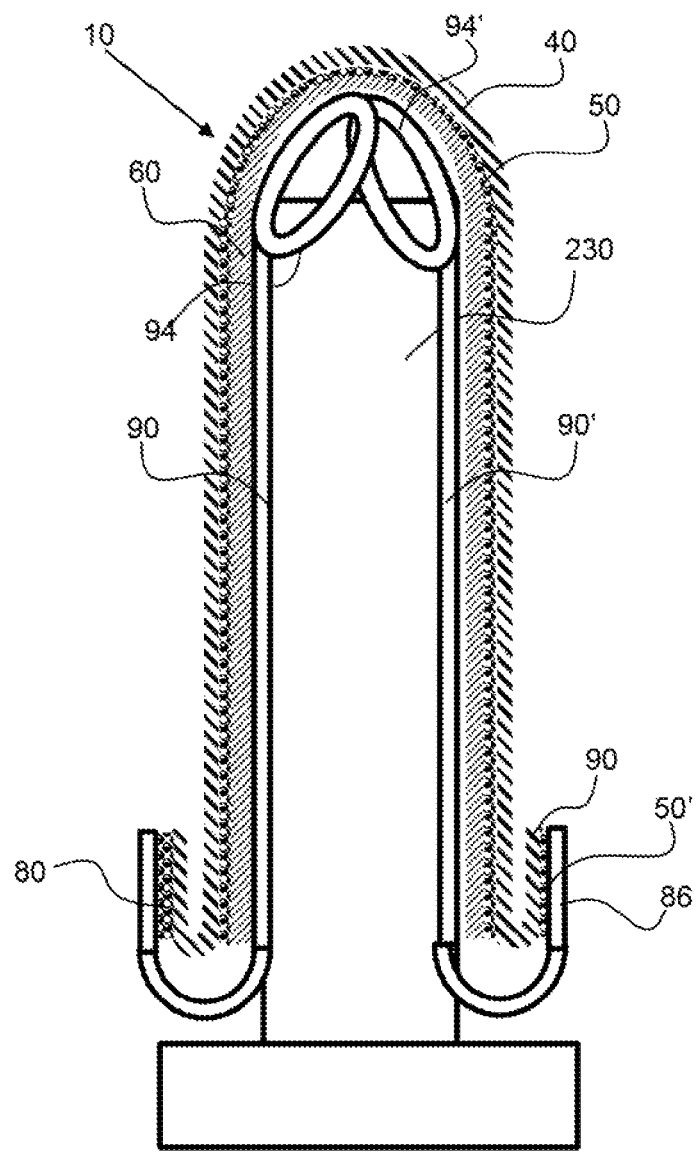
Figure 17:
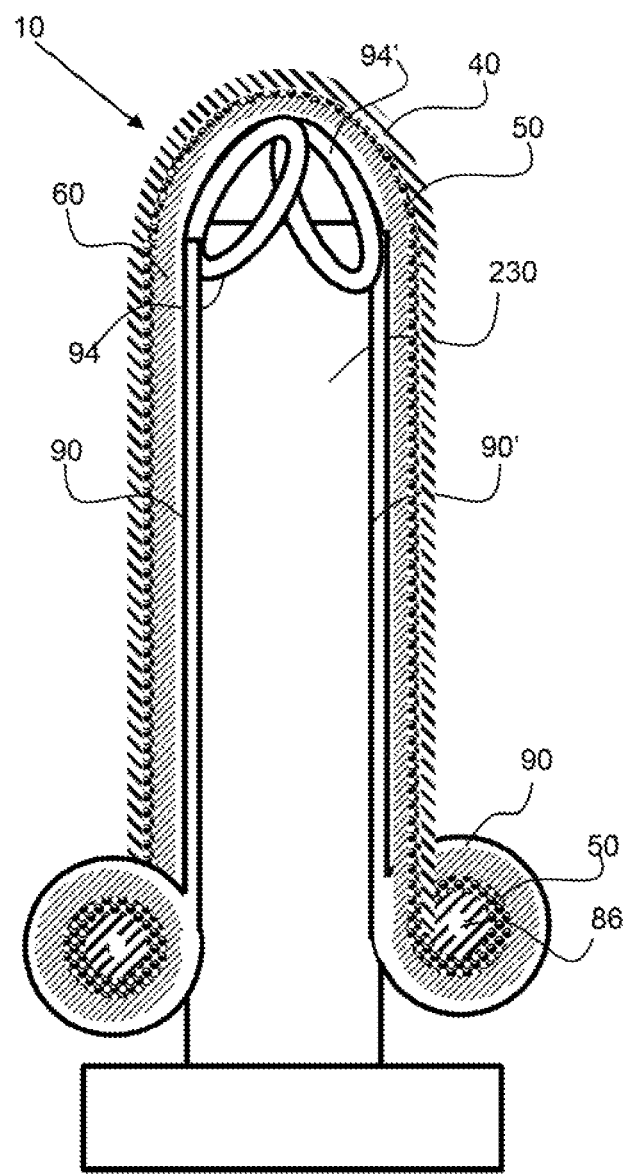

Referring now to FIGS. 12 to 16, an exemplary method of making an inverting digit bandage requires a multi-step method or process. As shown in FIG. 12, a form 230 is used to form the inverting digit bandage. A dressing 60 is applied to and covers the form, and then a bandage adhesive 50 is applied. However, a dressing may be configured on the form already having an adhesive. As shown in FIG. 13, an absorbent material 40 or portion is attached to the dressing by the adhesive. Note that the dressing layer extends down further than the absorbent material, as it will form the attachment tab. As shown in FIG. 14, the assembly shown in FIG. 13 is then inverted onto a second form 230'. The dressing 60 is now on the outside surface and the absorbent material 40 is on the inside surface, or faces the second form 230'. Note that the deployment strip 90 and deployment loop 94 are placed on the second form 230' before the assembly was inverted onto the second form. This step configures the deployment strip in the correct location for later use. As shown in FIG. 15, a portion of the extended end of the bandage, or the attachment tab 89, is inverted and adhesive 50' is applied. Note that adhesive may be applied to the dressing in FIG. 12 or 13, that extends to the attachment tab. However, the exposed adhesive has to be covered prior to inverting the bandage onto the second form 230'. As shown in FIG. 16, the deployment strip 90 and release layer 86 are attached to the attachment tab 80. The deployment strip may be coupled to the release layer prior to placement on the second form. Alternatively, the deployment strip and release layer may be attached prior to placement on the second form. With the release layer attached to the exposed adhesive 50', as shown in FIG. 16, the inverting digit bandage is ready to be rolled up, or inverted. The inverted digit bandage 10 shown in FIG. 17 produces an inverting digit bandage, as shown in FIG. 2, when inverted to expose the deployment loops and form a toroid portion 34.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An inverting digit bandage system comprising:
 a) an inverting digit bandage comprising:
  i) a top portion;
  ii) a sleeve portion coupled with the top portion and extending to an extended sleeve end;
  wherein the sleeve portion is rolled up into a toroid portion of a deployment toroid;
  iii) an absorbent layer,
  iv) a dressing layer;
  wherein the absorbent layer and dressing layer extended along the sleeve portion;
 b) a deployment strip comprising:
  i) a deployment tab;
  ii) a deployment extended end;
  iii) a length from the deployment tab to the deployment extended end;
  wherein the deployment tab extends out from the toroid portion;
  wherein the deployment strip is rolled up in the toroid portion with the deployment extended end within the toroid portion;
 c) a first and a second deployment strip;
 d) an attachment tab coupled to the extended end of the sleeve portion,
 wherein the attachment tab extends from the extended sleeve end to an extended attachment end;
 wherein the attachment tab comprises:
  an attachment adhesive for adhering to the digit to secure the inverting digit bandage to the digit; and
  a release layer configured over the attachment adhesive;
 wherein the first deployment strip is coupled to the attachment tab;
 wherein the first deployment strip is attached to the release layer of the attachment tab and wherein the release layer is removed from the attachment tab by pulling on the first deployment strip; and
 wherein the inverting digit bandage is deployed over a digit by placing the top portion over a distal end of said digit and pulling on the deployment tab to unwind the toroid portion over the digit, wherein the sleeve portion extends around a digit shaft.

2. The inverting digit bandage system of claim 1, further comprising an attachment tab coupled to the extended end of the sleeve portion;
 wherein the attachment tab extends from the extended sleeve end to an extended attachment end; and
 wherein the attachment tab comprises an attachment adhesive for securing the inverting digit bandage over the digit.

3. The inverting digit bandage system of claim 2, wherein the attachment tab comprises a release layer configured over the attachment adhesive, wherein the release layer is removed before the attachment tab is adhered.

4. The inverting digit bandage system of claim 3, wherein the deployment strip is attached to the release layer of the attachment tab and wherein the release layer is removed from the attachment tab by pulling on the deployment strip.

5. The inverting digit bandage system of claim 2, comprising two attachment tabs.

6. The inverting digit bandage system of claim 2, wherein the attachment tab is a discrete attachment tab.

7. The inverting digit bandage system of claim 1, wherein the absorbent layer is a discontinuous layer.

8. The inverting digit bandage system of claim 1, wherein the dressing layer is elastic.

9. The inverting digit bandage system of claim 1, wherein the first deployment strip is attached to a first release layer of a first attachment tab and wherein the second deployment strip is attached to a second release layer of a second attachment tab.

10. The inverting digit bandage system of claim 1, further comprising a vie ng window to evaluate a vascular status of the digit.

11. An inverting digit bandage system comprising:
a) an inverting digit bandage comprising:
  i) a top portion;
  ii) a sleeve portion coupled with the top portion and extending to an extended sleeved end;
  wherein the sleeve portion is rolled up into toroid portion of a deployment toroid;
  iii) an absorbent layer,
  iv) a dressing layer;
  wherein the absorbent layer and dressing layer extended along the sleeve portion;
b) a viewing window to evaluate a vascular status of the digit;
c) a deployment strip comprising:
  v) a deployment tab;
  vi) a deployment extended end;
  vii) a length from the deployment tab to the deployment extended end;
  wherein the deployment tab extends out from the toroid portion;
  wherein the deployment strip is rolled up in the toroid portion with the deployment extended end within the toroid portion;
wherein the inverting digit bandage is deployed over a digit by placing the top portion over a distal end of said digit and pulling on the deployment tab to unwind the toroid portion over the digit, wherein the sleeve portion extends around a digit shaft; and
wherein the viewing window is configured to align with a digit nail and wherein the deployment toroid comprises a window marking to indication a location of the viewing window along the circumference of the deployment toroid.

12. A method of inverting a bandage over a digit comprising the steps of:
a) providing an inverting digit bandage system comprising:
  i) an inverting digit bandage comprising:
    a top portion;
    a sleeve portion coupled with the top portion and extending to an extended sleeve end;
    wherein the sleeve portion is rolled up into a toroid portion of a deployment toroid;
    an absorbent layer,
    a dressing layer;
    wherein the absorbent layer and dressing layer extended along the sleeve portion;
  ii) deployment strip comprising:
    deployment tab;
    a deployment extended end:
    a length from the deployment tab to the deployment extended end;
    wherein the deployment tab extends out from the toroid portion;
    wherein the deployment strip is rolled up in the toroid portion with the deployment extended end within the toroid portion;
    wherein the inverting digit bandage is deployed over a digit by placing the top portion over a distal end of said digit and pulling on the deployment tab to unwind the toroid portion over the digit, wherein the sleeve portion extends around a digit shaft
b) placing the top portion over the extended end of the digit; pulling on the deployment strip while inverting the sleeve portion over the digit;
c) an attachment tab coupled to the extended end of the sleeve portion;
wherein the attachment tab extends from the extended sleeve end to an extended attachment end;
wherein the attachment tab comprises an attachment adhesive for securing the inverting digit bandage over the digit;
wherein the deployment strip is coupled to the attachment tab;
wherein the attachment tab comprises a release layer configured over the attachment adhesive, wherein the release layer is removed before the attachment tab is adhered to the digit; and
wherein the deployment strip is attached to the release layer of the attachment tabs and wherein the release layer is removed from the attachment tab by pulling on the deployment strip.

13. The method of inverting a bandage over a digit of claim 12, wherein the release layer has a plurality of discontinuities.

14. The method of inverting a bandage over a digit of claim 12, wherein the attachment tab extends only a portion around a circumference of the digit.

15. The method of inverting a bandage over a digit, of claim 12, wherein the absorbent layer is a discontinuous layer.

16. The method of inverting a bandage over a digit of claim 12, wherein the dressing layer is elastic.

17. The method of inverting a bandage over a digit of claim 12, comprising a first and a second deployment strip.

18. The method of inverting a bandage over a digit of claim 17, wherein the first deployment strip is configured on an opposing side of the inverting digit bandage from the second deployment strip.

19. The method of inverting a bandage over a digit of claim 12, further comprising a viewing window in the sleeve portion.

20. The method of inverting a bandage over a digit of claim 19, wherein the viewing window is configured to align with a digit nail and wherein the deployment toroid comprises a window marking to indicate a location of the viewing window along the circumference of the deployment toroid.

21. A method of inverting a bandage over a digit comprising the steps of:
a. providing an inverting digit bandage system comprising:
  i. an inverting digit bandage comprising:
    a top portion;

a sleeve portion coupled with the to portion and extending to an extended sleeve end:
wherein the sleeve portion is rolled up into a toroid portion of a deployment toroid;
an absorbent layer,
a dressing layer;
wherein the absorbent layer and dressing layer extended along the sleeve portion;
ii) a deployment strip comprising:
deployment tab;
a deployment extended end;
a length from the deployment tab to the deployment extended end;
wherein the deployment tab extends out from the toroid portion;
wherein the deployment strip is rolled up in the toroid portion with the deployment extended end within the toroid portion;
wherein the inverting digit bandage is deployed over a digit by placing the top portion over a distal end of said digit and pulling on the deployment tab to unwind the toroid portion over the digit, wherein the sleeve portion extends around a digit shaft b. placing the top portion over the extended end of the digit; pulling on the deployment strip while inverting the sleeve portion over the digit;

c) an attachment tab coupled to the extended end of the sleeve portion,
wherein the attachment tab extends from the extended sleeve end to an extended attachment end;
wherein the attachment tab comprises:
an attachment adhesive for adhering to the digit to secure the inverting digit bandage to the digit; and
a release layer configured over the attachment adhesive;
wherein the first deployment strip is coupled to the attachment tab;
wherein the first deployment strip is attached to the release layer of the attachment tab and wherein the release layer is removed from the attachment tab by pulling on the first deployment strip.

\* \* \* \* \*